(12) United States Patent
Sekine (10) Patent No.: US 11,908,474 B2
(45) Date of Patent: Feb. 20, 2024

(54) PRESENTATION EVALUATION SYSTEM (71) Applicant: INTERACTIVE SOLUTIONS CORP., Tokyo (JP)

(72) Inventor: Kiyoshi Sekine, Tokyo (JP)

(73) Assignee: Interactive Solutions Corp., Tokyo (JP)

( * ) Notice: Subject to any disclaimer, the term of this patent is extended or adjusted under 35 U.S.C. 154(b) by 0 days.

(21) Appl. No.: 18/013,905

(22) PCT Filed: Dec. 28, 2021

(86) PCT No.: PCT/JP2021/048987
§ 371 (c)(1),
(2) Date: Dec. 30, 2022

(87) PCT Pub. No.: WO2022/185705
PCT Pub. Date: Sep. 9, 2022

(65) Prior Publication Data
US 2023/0197074 A1 Jun. 22, 2023

(30) Foreign Application Priority Data
Mar. 2, 2021 (JP) ................................. 2021-032752

(51) Int. Cl.
*G10L 15/08* (2006.01)
*G10L 15/22* (2006.01)
*G06F 40/279* (2020.01)

(52) U.S. Cl.
CPC ............ *G10L 15/22* (2013.01); *G06F 40/279* (2020.01); *G10L 15/08* (2013.01); *G10L 2015/088* (2013.01)

(58) Field of Classification Search
CPC ............... G10L 15/22; G10L 2015/088; G06F 40/279
See application file for complete search history.

(56) References Cited

U.S. PATENT DOCUMENTS 7,739,116 B2 * 6/2010 Miyamoto .............. G10L 15/26
704/9
9,606,622 B1 * 3/2017 Brothers .................. G06F 3/013
(Continued)

FOREIGN PATENT DOCUMENTS

CA 3063019 C * 1/2021 ........... G06F 16/332
CN 107004428 A 8/2017
(Continued)

OTHER PUBLICATIONS

International Search Report of International Patent Application No. PCT/JP2021/048987 completed on Mar. 2, 2022 and dated Mar. 15, 2022 (4 pages).
(Continued)

*Primary Examiner* — Daniel C Washburn
*Assistant Examiner* — Oluwadamilola M Ogunbiyi
(74) *Attorney, Agent, or Firm* — Pyprus Pte Ltd; George D. Liu (57) ABSTRACT

[Problem] Provided is a system that can objectively evaluate a person who makes a presentation (presenter) [Solution] A presentation evaluation system 1 includes: a voice analysis unit 3 that analyzes a content of a conversation, a presentation material related information storage unit 5 that stores information related to a presentation material, a keyword storage unit 7 that stores information related to a keyword in each page of the presentation material, a related term storage unit 9 that stores a related term of each keyword, and an evaluation unit 11 that evaluates the content of the conversation analyzed by the voice analysis unit 3 or a person who had the conversation. The presentation evaluation system 1 evaluates the content of the conversation or the person who had the conversation based on a count of keywords of each page of the presentation material included in the content of the conversation analyzed by the voice analysis unit 3, a (Continued)

count of related terms, a combination of keywords, or a combination of related terms.

6 Claims, 4 Drawing Sheets

(56) References Cited

U.S. PATENT DOCUMENTS

| | | | | |
|---|---|---|---|---|
| 2009/0154810 | A1* | 6/2009 | Enomoto | G06V 30/287 382/182 |
| 2009/0265344 | A1* | 10/2009 | Etoh | G06F 16/951 707/999.005 |
| 2014/0089418 | A1* | 3/2014 | Davenport | H04L 51/216 709/206 |
| 2014/0278613 | A1* | 9/2014 | Suzuki | G06Q 50/12 705/5 |
| 2014/0362738 | A1* | 12/2014 | Neystadt | H04M 3/42221 704/235 |
| 2014/0365866 | A1* | 12/2014 | Kinoshita | G06F 16/951 715/234 |
| 2015/0036167 | A1* | 2/2015 | Naitoh | G06F 3/1239 358/1.14 |
| 2017/0011743 | A1* | 1/2017 | Matsumoto | G10L 15/30 |
| 2017/0351747 | A1* | 12/2017 | Morimoto | G06F 16/00 |
| 2018/0277009 | A1* | 9/2018 | Kojo | G09B 5/12 |
| 2019/0087420 | A1* | 3/2019 | Dunnington | G06F 16/93 |
| 2021/0182325 | A1* | 6/2021 | Krishnan | G06F 16/34 |
| 2022/0270500 | A1* | 8/2022 | Tsunashima | G06Q 10/0639 |

FOREIGN PATENT DOCUMENTS

| | | |
|---|---|---|
| CN | 107851097 A | 3/2018 |
| CN | 111835529 A | 10/2020 |
| JP | 2002-259635 A1 | 9/2002 |
| JP | 2017-224052 A1 | 12/2017 |
| JP | 2019078924 A | 5/2019 |
| JP | 2020-119112 A | 8/2020 |
| JP | 2020-190579 A | 11/2020 |

OTHER PUBLICATIONS

Written Opinion of International Patent Application No. PCT/JP2021/048987 completed on Mar. 2, 2022 and dated Mar. 15, 2022 (3 pages).

Office Action of Chinese application No. 202180034839.5 dated Mar. 17, 2023 (8 pages).

* cited by examiner

PRESENTATION EVALUATION SYSTEM

TECHNICAL FIELD

This invention relates to a presentation evaluation system.

BACKGROUND ART

Patent Document 1 discloses a system that displays a keyword with the combination of a graphic object and a text out of a statement in the process of discussion by participants of the discussion.

Patent Document 2 discloses a presentation support device using a voice analysis terminal.

Patent Document 1: JP-A-2002-259635
Patent Document 2: JP-A-2017-224052

DISCLOSURE OF THE INVENTION

Problems to be Solved by the Invention

A system that can objectively evaluate a person who makes a presentation (presenter), divide a plurality of presenters into categories, or determine which page of a presentation including a plurality of pages is efficient to use for evaluating a presenter is desired. An object of one of inventions described in this description is to solve any one of the above problems.

Solutions to the Problems

One of the inventions described in this description is based on a knowledge that a page that is efficient for evaluating a presenter can be easily found through counts and combinations of keywords and related terms, and a grouping.

One invention relates to a presentation evaluation system 1. The presentation evaluation system 1 includes a voice analysis unit 3, a presentation material related information storage unit 5, a keyword storage unit 7, a related term storage unit 9, and an evaluation unit 11.

The presentation evaluation system 1 is, for example, a system supported by a computer that evaluates a presentation by a presenter.

The voice analysis unit 3 is an element for analyzing a content of a conversation.

The presentation material related information storage unit 5 is an element for storing information related to a presentation material.

The keyword storage unit 7 is an element for storing information related to a keyword in each page of the presentation material.

The related term storage unit 9 is an element for storing a related term of each keyword described above.

The evaluation unit 11 is an element for evaluating the content of the conversation analyzed by the voice analysis unit 3 or a person who had the conversation. Based on a count of keywords, a count of related terms, a combination of the keywords, or a combination of the related terms in each page of the presentation material included in the content of the conversation analyzed by the voice analysis unit, the evaluation unit 11 evaluates the content of the conversation or the person who had the conversation.

With the above invention, the content of a conversation or a person who had the conversation can be evaluated based on the counts or the combinations of keywords and related terms. When the content of a conversation or a person who had the conversation is evaluated using only the keywords, a case of using the related terms which have meanings substantially identical to those of the keywords is not justly evaluated. Therefore, by evaluating the content of a conversation or a person who had the conversation based on the counts or the combinations of keywords and related terms, the evaluation can be performed with higher accuracy. For example, the evaluation unit 11 may obtain an evaluation value based on the counts or the combinations of keywords and related terms. Then, based on the obtained evaluation value, the content of a conversation or a person who had the conversation may be evaluated. The keywords and the related terms may be multiplied by coefficients such that the evaluation value becomes higher when the keywords are used. The evaluation value may be configured to become higher when a specific related term is used than when other related terms are used.

According to another invention that is different from the above described in this description, based on a count or a combination of keywords or related terms of each page (specifically, a count or a combination of related terms), the content of a conversation or a person who had the conversation is evaluated.

Preferably, the above presentation evaluation system 1 further includes a grouping unit 13. The grouping unit 13 is an element for dividing persons who had a conversation into groups based on counts or combinations of keywords and related terms of each page of the presentation material included in the content of a conversation analyzed by the voice analysis unit 3

Since this invention further includes the grouping unit 13, presenters can be effectively divided into groups based on, for example, evaluation values.

Preferably, the above presentation evaluation system 1 further includes a page extracting unit 15. The page extracting unit 15 is an element for extracting an evaluation page that is a page of a presentation material for evaluating, for the groups divided by the grouping unit 13, the content of a conversation or persons who had a conversation using a count or a combination of keywords or related terms of each page of the presentation material.

Since this invention includes the page extracting unit 15, the evaluation page appropriate for evaluating the presenters can be extracted. A presentation material may have one evaluation page or two or more evaluation pages.

Preferably, in the above presentation evaluation system 1, the keyword storage unit 7 further stores keyword appearance order information related to an appearance order of the keywords. In addition, as a preferred example, the keyword storage unit 7 further stores keyword combination order information related to a combination order of the keywords. Then, using the information related to the counts or the combinations of keywords and related terms in the evaluation page and the keyword appearance order or combination order information in the evaluation page, which are included in the content of a conversation analyzed by the voice analysis unit 3, the evaluation unit 11 evaluates the content of the conversation or the person who had the conversation. In this case, for example, an evaluation value may be acquired using the information related to the counts or the combinations of keywords and related terms in the evaluation page and the keyword appearance order or combination order information in the evaluation page, and the content of the conversation or the person who had the conversation may be evaluated using the evaluation value.

Note that the system 1 may evaluate the content of a conversation or a person who had the conversation using the counts or the combinations of keywords and related terms of each page of the presentation material included in the content of the conversation analyzed by the voice analysis unit and the keyword appearance order or combination order information in each page of the presentation material. Furthermore, the evaluation value may be acquired even if a page moves to a different page without using the keyword or the related term in the evaluation page and returns to the evaluation page to use the keyword or the related term that should be originally used.

Preferably, the above presentation evaluation system 1 further includes an evaluation keyword extracting unit 17, an unused evaluation keyword extracting unit 19, and an unused evaluation keyword output unit 21.

The evaluation keyword extracting unit 17 is an element for extracting a keyword used related to the evaluation page as an evaluation keyword, in the group having a highest count of keywords, a highest count of related terms, a highest count of combinations of keywords, or a highest count of combinations of related terms of each page of the presentation material, among the groups divided by the grouping unit.

The unused evaluation keyword extracting unit 19 is an element for extracting an unused evaluation keyword. The unused evaluation keyword is a keyword included in the content of a conversation analyzed by the voice analysis unit 3 and a keyword that is not included in terms included in the conversation in the evaluation page.

The unused evaluation keyword output unit 21 is an element for outputting the unused evaluation keyword extracted by the unused evaluation keyword extracting unit 19.

Furthermore, throughout the entire presentation material, from the count or combination of keywords or related terms that are frequently used or less frequently used, a trend of a presenter's strong points or weak points may be presented, or the keywords or related terms that should be used may be recommended.

Advantageous Effects of the Invention

With the invention described in this description, for example, a person who makes a presentation (presenter) can be objectively evaluated, a plurality of presenters can be divided into categories, or which page of a presentation including a plurality of pages is efficient to use for evaluating a presenter can be determined.

DESCRIPTION OF PREFERRED EMBODIMENTS

The following describes embodiments of the present invention using the drawings. The present invention is not limited to the embodiments described below, but includes modifications from the following embodiments appropriately made by those skilled in the art within the obvious scope.

Figure 1:
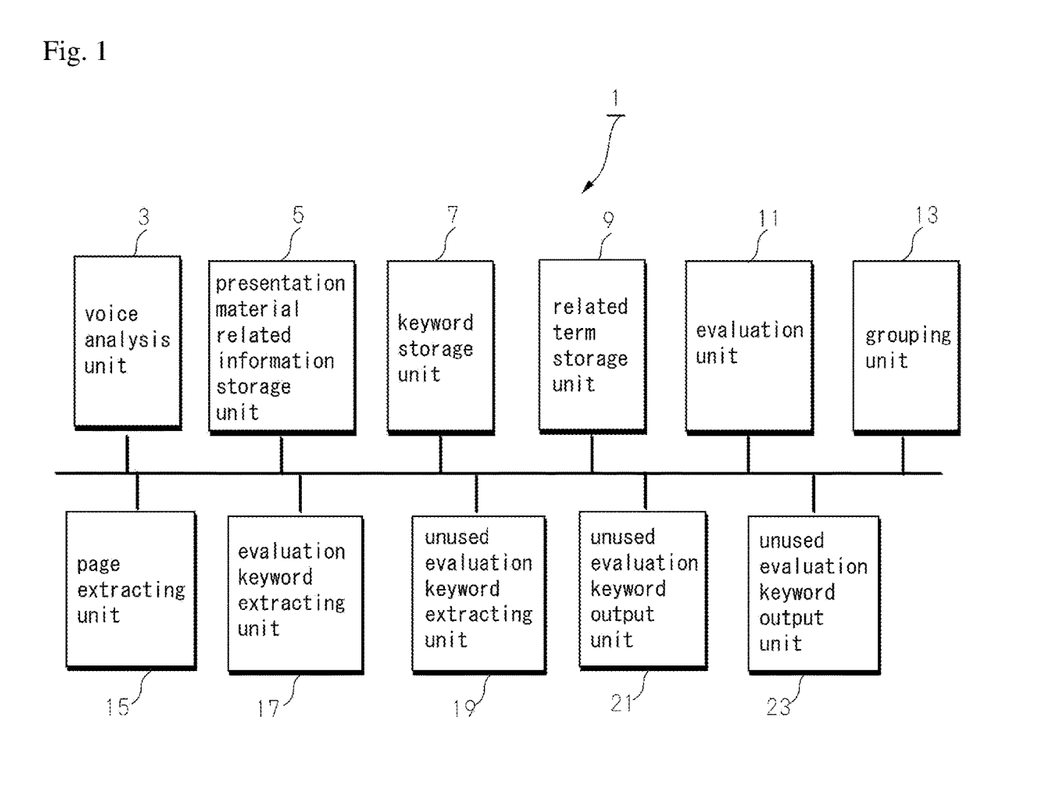
FIG. 1 is a block diagram for describing a system of the present invention.

FIG. 1 is a block diagram for describing a system of the present invention. One invention described in this description relates to a presentation evaluation system 1. This system includes a computer, and each element described below is an element implemented by the computer. The computer may be any of various terminals, a mobile terminal, a notebook computer, a personal computer, a server, and a computer server system. This system may be implemented by a processor or may be implemented by cooperation of various hardware and software, such as a program.

As illustrated in FIG. 1, the presentation evaluation system 1 includes a voice analysis unit 3, a presentation material related information storage unit 5, a keyword storage unit 7, a related term storage unit 9, and an evaluation unit 11. The system further includes any one or two or more elements of a grouping unit 13, a page extracting unit 15, an evaluation keyword extracting unit 17, an unused evaluation keyword extracting unit 19, and an unused evaluation keyword output unit 21.

Figure 2:
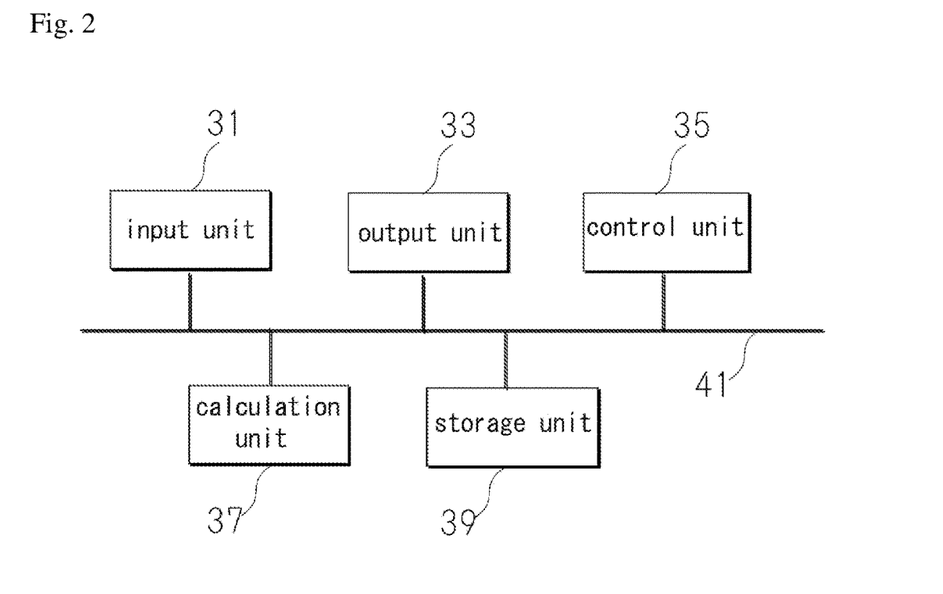
FIG. 2 is a block diagram illustrating a basic configuration of a computer.

FIG. 2 is a block diagram illustrating a basic configuration of the computer. As illustrated in this drawing, the computer has an input unit 31, an output unit 33, a control unit 35, a calculation unit 37, and a storage unit 39, and each element is connected by, for example, a bus 41 so as to be able to transmit and receive information. For example, in the storage unit, a control program may be stored, or various information may be stored. When predetermined information is input from the input unit, the control unit reads out the control program stored in the storage unit. Then, the control unit reads out the information stored appropriately in the storage unit and transmits it to the calculation unit. Further, the control unit transmits the information input appropriately to the calculation unit. The calculation unit conducts a computation process using the received various information, and stores the resultant in the storage unit. The control unit reads out the result of the computation process stored in the storage unit and outputs it from the output unit. Various processes are thus conducted. Each element described below may correspond to any of the elements of the computer. Examples of the output unit include a monitor and a screen.

Figure 3:
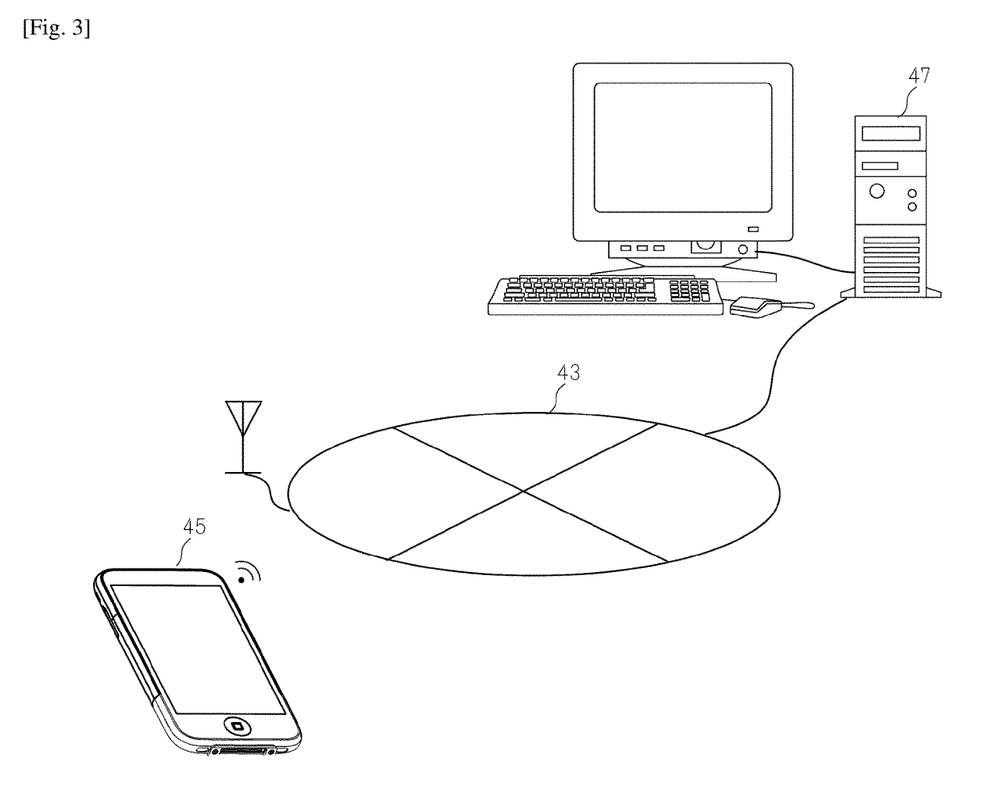
FIG. 3 is a conceptual diagram illustrating an example of the system of the present invention.

FIG. 3 is a conceptual diagram illustrating an example of the system of the present invention. As illustrated in FIG. 3, the system of the present invention (the system including a device of the present invention) may be a system including a mobile terminal 45 connected to the Internet or intranet 43 and a server 47 connected to the Internet or intranet 43. Surely, a single computer or mobile terminal may function as the device of the present invention, or a plurality of servers may exist.

Presentation Evaluation System 1

The presentation evaluation system 1 is, for example, a system supported by a computer and used for evaluating the content of a conversation or a person who had the conversation (for example, a presentation by a presenter). This system obtains, for example, an index referred to as an evaluation value, and evaluates the content of a conversation or a person who had the conversation using the index. Examples of the conversation include a conversation between an MR and a doctor, a conversation between a patient and a medical doctor, and a presentation. That is, the conversation may be that being bidirectional or that being one-directional.

Voice Analysis Unit 3

The voice analysis unit 3 is an element for analyzing the content of a conversation, and for example, analyzes words included in the conversation and acquires conversation information.

For example, via a microphone, a voice is input to the presentation evaluation system. Then, the presentation evaluation system stores the conversation (voice) in a storage unit. The voice analysis unit 3 reads out the conversation (voice) from the storage unit, analyzes the words included in the conversation, and acquires the conversation information. An example of the conversation information is a modification of the voice into sound information. The presentation evaluation system has a database in which candidates of conversion words for converting words and phrases included in a conversational sentence are stored and may convert the conversation using the candidates of the conversion words.

Presentation Material Related Information Storage Unit 5

The presentation material related information storage unit 5 is an element for storing information related to a presentation material.

For example, the storage unit of the computer functions as the presentation material related information storage unit 5. An example of the presentation material is each page of PowerPoint (registered trademark). The presentation material may be a material of PowerPoint or the like including a plurality of pages. That is, the presentation material may be a set of a sequence of page candidates including a plurality of display elements that are displayed as a presentation. The presentation material is a material that is housed in the computer and displayed on a display unit so as to ensure making a presentation to a speaker oneself, an opposite party of a conversation, or an audience.

The presentation material related information includes, for example, any or both of presentation specific information that is information for identifying a specific presentation material and page specific information for identifying each page of the presentation material.

Examples of the presentation material related information include, in addition to the content of the presentation described above, a presentation identification number (ID) for calling up the presentation, page number information, presentation category information, a tag related to the presentation, keywords related to the presentation, presentation preparer information, dates prepared and updated of the presentation, presentation security information, and information related to presentation software.

Keyword Storage Unit 7

The keyword storage unit 7 is an element for storing information related to a keyword in each page of the presentation material. For example, the storage unit of the computer functions as the keyword storage unit 7. An example of a plurality of keywords associated with the presentation material is terms that are possibly used when an explanation is performed based on each page of PowerPoint. The storage unit houses the plurality of keywords in association with each page of the presentation material of PowerPoint or the like. In association with the information (for example, a file ID or page number) of the presentation material, the storage unit stores the plurality of keywords associated with the presentation material. Examples of a keyword include "diabetes," "new drug," "XYZ," "ABC" (names of other therapeutic agents), "blood glucose level," "side effect," "blood sugar," "glaucoma," "retinopathy," "insulin," "DC Pharmaceutical," "side effect," and "package insert."

Related Term Storage Unit 9

The related term storage unit 9 is an element for storing a related term of each keyword described above. For example, the storage unit of the computer functions as the related term storage unit 9. The related term is a term that is not identical to a keyword but is associated with the keyword. The related term may be a term that is not identical to a keyword but is possibly used in a conversation as a term intended as the keyword. Examples of the related term include synonyms and quasi-synonyms of a keyword. For example, in relation to the keyword "diabetes," the examples are "Type I," "Type II," "lifestyle-related disease," "metabolic disorder," and "insulin." In the related term storage unit 9, a plurality of dictionaries may be disposed for each category. Then, when tag information is stored in association with the presentation material information (for example, a file ID and page number), an appropriate dictionary in the related term storage unit 9 may be selected using the tag information, and the related term may be read out using the selected related term dictionary.

The evaluation unit 11 is an element for evaluating the content of a conversation or a person who had the conversation analyzed by the voice analysis unit 3. Based on a count of keywords, a count of related terms, a combination of the keywords, or a combination of the related terms in each page of the presentation material included in the content of the conversation analyzed by the voice analysis unit, the evaluation unit 11 evaluates the content of the conversation or the person who had the conversation. For example, the storage unit, the calculation unit, and the control unit of the computer function as the evaluation unit 11. In this case, for example, it is only necessary to store a program in the storage unit, obtain an evaluation value based on a command of the program, and evaluate the content of the conversation or the person who had the conversation using the evaluation value. As a preferred example, based on the count of keywords and the count of related terms of each page of the presentation material included in the content of a conversation analyzed by the voice analysis unit, the evaluation unit 11 evaluates the content of the conversation or the person who had the conversation.

For example, the evaluation unit 11 reads out the conversation information from the storage unit. Then, for example, using each presentation material and its page ID and page information, the evaluation unit 11 reads out the information related to the keyword in each page of the presentation material from the keyword storage unit 7. Then, using the read information related to the keyword, the evaluation unit 11 reads out the related term of each keyword from the related term storage unit 9. Subsequently, the evaluation unit 11 conducts a computation process to examine if the keyword and the related term are included in the conversation information read out from the storage unit. Then, for example, for each page of the presentation material, the keyword included in the conversation, the count of keywords, the related term, and the count of related terms are stored in the storage unit. For example, each keyword and related term are assigned with an individual evaluation value, and the evaluation unit 11 combines the individual evaluation values to obtain an evaluation value for each page and an evaluation value for the entire presentation. The evaluation unit 11 stores the obtained various evaluation values in the storage unit.

With the above invention, the content of a conversation or a person who had the conversation can be evaluated based on the counts of keywords and related terms. When the content of a conversation or a person who had the conversation is evaluated using only the keywords, a case of using the related terms which have meanings substantially identical to those of the keywords is not justly evaluated. Therefore, by evaluating the content of a conversation or a person who had the conversation based on the counts of keywords and related terms, the evaluation can be performed with higher accuracy. For example, the evaluation unit 11 may obtain the evaluation value based on the combination of keywords and the combination of related terms. In this case, the evaluation value may be obtained based on a count of combinations of keywords and a count of combinations of related terms. Then, based on the obtained evaluation value, the content of a conversation or a person who had the conversation may be evaluated. The keywords and the related terms (or the combinations thereof) may be multiplied by coefficients such that the evaluation value becomes higher when the keywords are used. The evaluation value may be configured to become higher when a specific related term is used than when other related terms are used. Furthermore, the evaluation value may be configured to become higher when a predetermined combination is included.

According to another invention that is different from the above described in this description, based on the count of keywords, the count of related terms, the combination of keywords, or the combination of related terms of each page (specifically, the count of related terms or the combination of related terms), the content of a conversation or a person who had the conversation is evaluated.

Preferably, the above presentation evaluation system 1 further includes the grouping unit 13. The grouping unit 13 is an element for dividing persons who had a conversation into groups based on the count of keywords, the count of related terms, the combination of keywords, or the combination of related terms of each page of the presentation material included in the content of a conversation analyzed by the voice analysis unit 3.

Since this invention further includes the grouping unit 13, presenters (persons having a conversation) can be effectively divided into groups based on, for example, evaluation values. For example, the storage unit stores how many groups to be divided into. The system may read out information related to a count of groups and divide the presenters into groups based on the evaluation values. In addition, the system may store a relationship between evaluation values and groups and assign the presenters to corresponding groups based on the evaluation values.

Preferably, the above presentation evaluation system 1 further includes the page extracting unit 15. The page extracting unit 15 is an element for extracting the evaluation page that is a page of a presentation material for evaluating, for the groups divided by the grouping unit 13, the content of a conversation or persons who had a conversation using the count of keywords, the count of related terms, the combination of keywords, or the combination of related terms of each page of the presentation material.

Since this invention includes the page extracting unit 15, the evaluation page appropriate for evaluating the presenters can be extracted. A presentation material may have one evaluation page or two or more evaluation pages.

As another aspect of the above system, based on the count of keywords and the count of related terms of each page of the presentation material included in the content of a conversation analyzed by the voice analysis unit, the evaluation unit 11 evaluates the content of the conversation or persons who had the conversation. The grouping unit 13 of this aspect divides the persons who had the conversation into groups based on the count of keywords and the count of related terms. The page extracting unit 15 of this aspect extracts the evaluation page for the groups divided by the grouping unit 13 using the count of keywords and the count of related terms.

As another aspect of the above system, the system includes the voice analysis unit 3, the presentation material related information storage unit 5, the keyword storage unit 7, the evaluation unit 11, the grouping unit 13, and the page extracting unit 15. The evaluation unit 11 of this aspect evaluates the content of a conversation or persons who had a conversation based on the count of keywords or the combination of keywords of each page of the presentation material included in the content of the conversation analyzed by the voice analysis unit 3. The grouping unit 13 of this aspect divides the persons who had the conversation into groups based on the count of keywords or the combination of keywords. The page extracting unit 15 of this aspect extracts the evaluation page for the groups divided by the grouping unit 13 using the count of keywords or the combination of keywords. In this aspect, grouping may be performed based only on the count of keywords to extract the evaluation page.

Thus, this system may appropriately use one or two or more among the count of keywords, the count of related terms, the combination of keywords, and the combination of related terms of each page of the presentation material, and still other elements to obtain the evaluation values, evaluates the content of a conversation or persons who had a conversation based on the evaluation values, divide them into groups, and extract the evaluation page.

Preferably, in the above presentation evaluation system 1, the keyword storage unit 7 further stores keyword appearance order information related to an appearance order of the keywords. Then, using the information related to the counts of keywords and related terms in the evaluation page and the keyword appearance order information in the evaluation page, which are included in the content of a conversation analyzed by the voice analysis unit 3, the evaluation unit 11 evaluates the content of the conversation or the person who had the conversation. In this case, for example, an evaluation value may be acquired using the information related to the counts of keywords and related terms in the evaluation page and the keyword appearance order information in the evaluation page, and the content of the conversation or the person who had the conversation may be evaluated using the evaluation value.

Note that the system 1 may evaluate the content of a conversation or a person who had the conversation using the counts or the combinations of keywords and related terms of each page of the presentation material included in the content of the conversation analyzed by the voice analysis unit and the keyword appearance order or combination order information in each page of the presentation material.

Preferably, the above presentation evaluation system 1 further includes the evaluation keyword extracting unit 17, the unused evaluation keyword extracting unit 19, and the unused evaluation keyword output unit 21.

The evaluation keyword extracting unit 17 is an element for extracting a keyword used related to the evaluation page as an evaluation keyword, in the group having the highest count or combination of keywords and related terms of each page of the presentation material among the groups divided by the grouping unit.

The unused evaluation keyword extracting unit 19 is an element for extracting an unused evaluation keyword. The unused evaluation keyword is a keyword included in the content of a conversation analyzed by the voice analysis unit 3 and a keyword that is not included in terms included in the conversation in the evaluation page.

The unused evaluation keyword output unit 21 is an element for outputting the unused evaluation keyword extracted by the unused evaluation keyword extracting unit 19.

For example, the system may be configured to delete an unused evaluation keyword from keywords for evaluation when the unused evaluation keyword output unit 21 outputs the unused evaluation keyword. By thus configuring, the system can reduce a count of keyword matching and perform the evaluation of a conversation or a person having a conversation quickly.

This invention includes a program for causing a computer to function as any of the systems described above and an information recording medium (such as, DVD, CD-ROM, USB flash drive, hard disk, and SIM card) that houses such a program and from the computer can read.

EXAMPLES

The following describes this invention in detail using examples. However, this invention is not limited to the following examples, but includes those appropriately modified based on publicly known elements.

In this example, a project manager (PM) of one company has registered slides in a system. In other words, one slide group was input to the system, and the system stores the slide set in a storage unit.

The PM set keywords for voice recognition for each page of the slide set. In other words, the system is configured to input the keywords for voice recognition for each page of the input slide set. The system stored the input keywords in the storage unit in association with each page of the slide set.

Presenters (in this example, 200 medical representatives (MRs)) made a presentation using respective terminals based on the slide set. Each terminal has a voice terminal (microphone), and voice of a presentation is input to the system. The following process may be conducted by each terminal, or various computations may be conducted by a server that can communicate with each terminal. In addition, a camera may be installed in each terminal to film a video and input the video to the system. In the video, the presenters may be filmed, or an audience (such as, medical doctors who receives explanations from the MRs) may be filmed. At any rate, the voice or video is input to the system via an input unit. The input voice or video may be stored in the storage unit.

A voice analysis unit of the system analyzed contents of conversations (presentations). The system read out the keywords in each page of the slide set and performed grouping by how many of the set keywords were used of each page. The grouping based on results of the presenters was as illustrated in Table 1. The grouping used was a grouping in descending order of speaking rate of the keywords in the entire slide set. The grouping was performed such that persons who had a high speaking rate (spoke the keywords often) belonged to group 7 and persons who had a low speaking rate belonged to group 1. The speaking rate is a rate taking the average of how many percent of the set keywords was spoken by members included in a group. In Table 1, how many percent of the keywords in all pages was spoken was defined as the speaking rate. There may be a database related to the presenters, in which the grouping performed based on the results of the presenters may be stored.

TABLE 1

| Group | 1 | 2 | 3 | 4 | 5 | 6 | 7 |
|---|---|---|---|---|---|---|---|
| Count of persons | 19 | 26 | 42 | 38 | 34 | 28 | 11 |

The count of keywords of each page and the speaking rate of the keywords for each group were as illustrated in Table 2 below. In Table 2, how many percent of the keywords in each page was spoken was defined as the speaking rate.

TABLE 2

| Page | Count of keywords | 1 | 2 | 3 | 4 | 5 | 6 | 7 |
|---|---|---|---|---|---|---|---|---|
| 2 | 12 | 2.00% | 14.30% | 31.50% | 58.40% | 52.00% | 55.60% | 65.30% |
| 3 | 9 | 3.10% | 18.10% | 37.00% | 60.70% | 55.50% | 57.10% | 65.70% |
| 4 | 5 | 0.30% | 11.60% | 18.20% | 43.90% | 56.80% | 58.90% | 78.60% |
| 5 | 10 | 2.50% | 14.20% | 35.70% | 66.60% | 64.20% | 85.60% | 92.90% |
| 6 | 7 | 0.00% | 4.80% | 7.80% | 14.60% | 38.10% | 39.60% | 59.50% |
| 7 | 4 | 0.00% | 2.40% | 12.90% | 19.20% | 35.10% | 33.90% | 42.50% |
| 8 | 1 | 0.00% | 3.80% | 10.80% | 16.20% | 28.60% | 43.80% | 59.10% |
| 9 | 5 | 1.70% | 3.40% | 13.20% | 23.50% | 33.90% | 62.90% | 54.60% |
| 10 | 3 | 0.00% | 11.30% | 15.50% | 25.00% | 28.60% | 68.60% | 48.80% |
| 11 | 7 | 1.20% | 5.30% | 11.50% | 19.20% | 42.40% | 61.80% | 68.70% |
| 12 | 6 | 2.40% | 20.80% | 27.70% | 45.20% | 48.90% | 41.60% | 49.60% |
| 13 | 10 | 0.00% | 0.00% | 3.50% | 8.90% | 22.10% | 62.40% | 63.30% |
| 14 | 4 | 0.00% | 20.60% | 25.40% | 45.60% | 53.70% | 46.90% | 61.70% |
| 15 | 2 | 0.00% | 12.30% | 19.80% | 32.30% | 38.80% | 42.00% | 44.90% |
| 16 | 3 | 0.40% | 14.30% | 23.70% | 34.30% | 41.40% | 52.20% | 53.40% |
| 17 | 6 | 1.20% | 18.10% | 16.10% | 26.50% | 26.30% | 32.50% | 51.80% |
| 18 | 9 | 0.00% | 1.20% | 7.80% | 12.80% | 27.70% | 55.60% | 51.60% |
| 19 | 4 | 1.70% | 13.30% | 19.60% | 34.60% | 42.80% | 72.70% | 79.90% |
| 20 | 7 | 2.90% | 21.90% | 38.20% | 65.30% | 75.10% | 93.90% | 92.40% |

As illustrated in Table 2, it was found that page 13 and page 18 showed a trend similar to that of an overall grouping. The system performs the overall grouping, and afterwards, performs the grouping for each page. Then, a page in which a trend of grouping (a group with a larger value has a higher evaluation value and speaking rate) agrees may be extracted as an evaluation target page. This system determined page 13 and page 18 as the evaluation target pages (evaluation pages) and stored them in the storage unit. Thus, it is preferred that an evaluation target page is determined because, once the evaluation target page is determined, the excellence of presenters can be evaluated only by evaluating the speaking rate of the keywords in the evaluation target page, without analyzing all the information on the slide set for the evaluation that follows.

For each keyword, related terms may be stored, and it may be interpreted that the associated keyword is spoken when the related terms are spoken. For example, for a fatal case that is desired to be highlighted, a keyword "no (nai in Japanese)" may have related terms, such as "nothing (nashi in Japanese)," "without (naku in Japanese)," and "there is no (arimasen in Japanese)," and those related terms may be stored in the system. The related terms may be automatically read out when the keyword "no (nai in Japanese)" is input to the system. When it is analyzed that the related terms exist in a conversation, the keyword may be automatically processed as having been spoken.

In this example, based on the count of keywords, the speaking rates were obtained to evaluate the presenters. The content of a conversation and persons who had a conversation may be evaluated by obtaining not the speaking rates but the evaluation values. In an example of the evaluation values, whether or not the related terms as well as the keywords have been spoken is analyzed, and the evaluation values are obtained from scores that have been assigned to the respective keywords and related terms. In addition, the evaluation values may be those based on the counts of keywords and related terms. Furthermore, for example, when a combination of keywords and a combination of related terms (such as, "diabetes" and "improvement," "drug A" (name of a drug) and "attached document") are included in a conversation, a high value may be provided.

Figure 4:
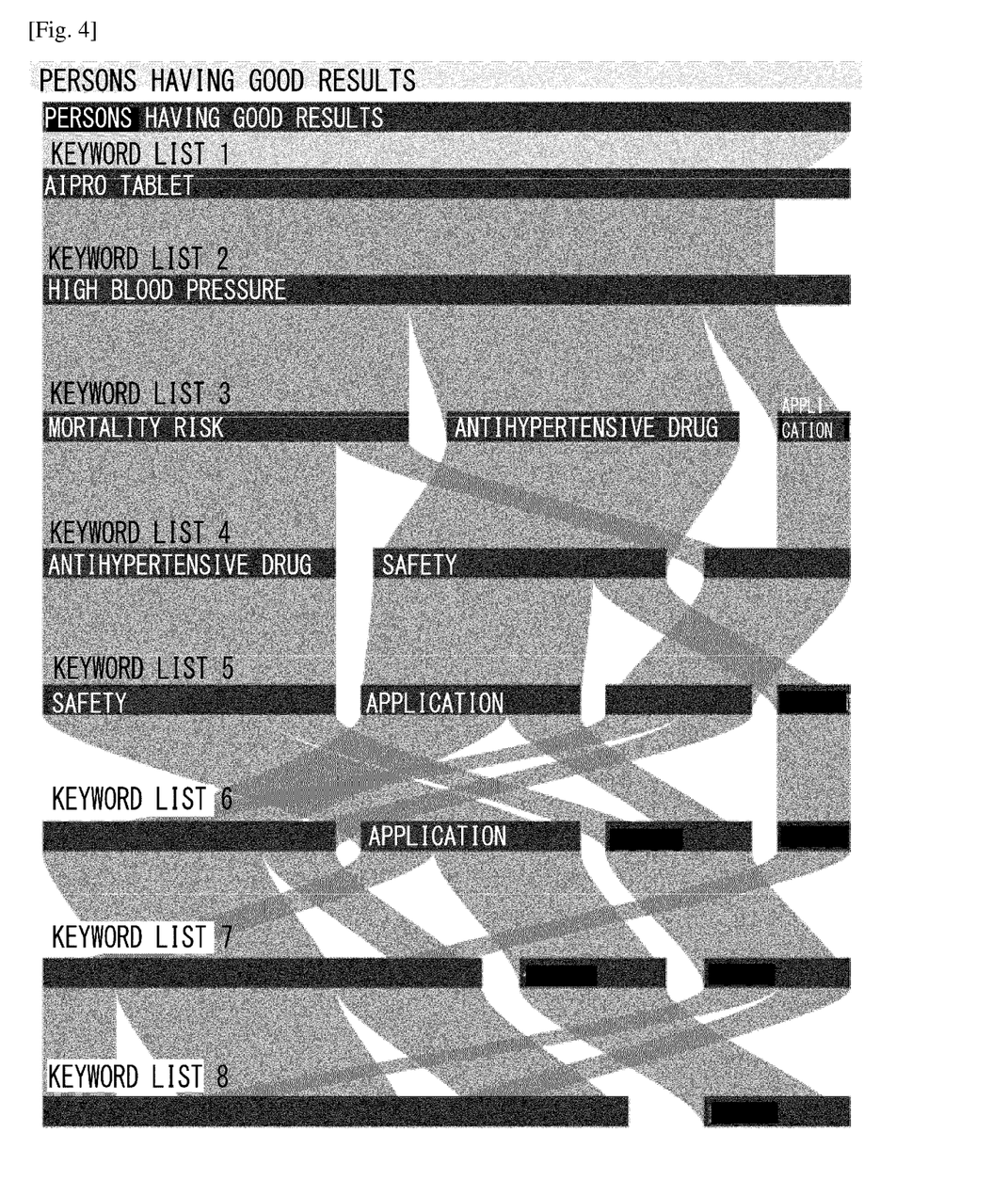
FIG. 4 is a conceptual diagram for describing a registration order of keywords by persons having good results.

FIG. 4 is a conceptual diagram for describing a registration order of keywords by persons having good results. As illustrated in FIG. 4, it was found that the persons having good results have not only high speaking rates of the respective keywords but also regularity about the order of using the keywords. Therefore, numerical values may be stored according to the registration order of the keywords so as to, for example, add points when keyword B comes after keyword A and further add points when keywords A, B, and C come in this order, and the evaluation value may be obtained by adding the numerical values. The evaluation value may be obtained by adding the numerical values when keyword groups C and D come after keyword groups A and B.

Figure 5:
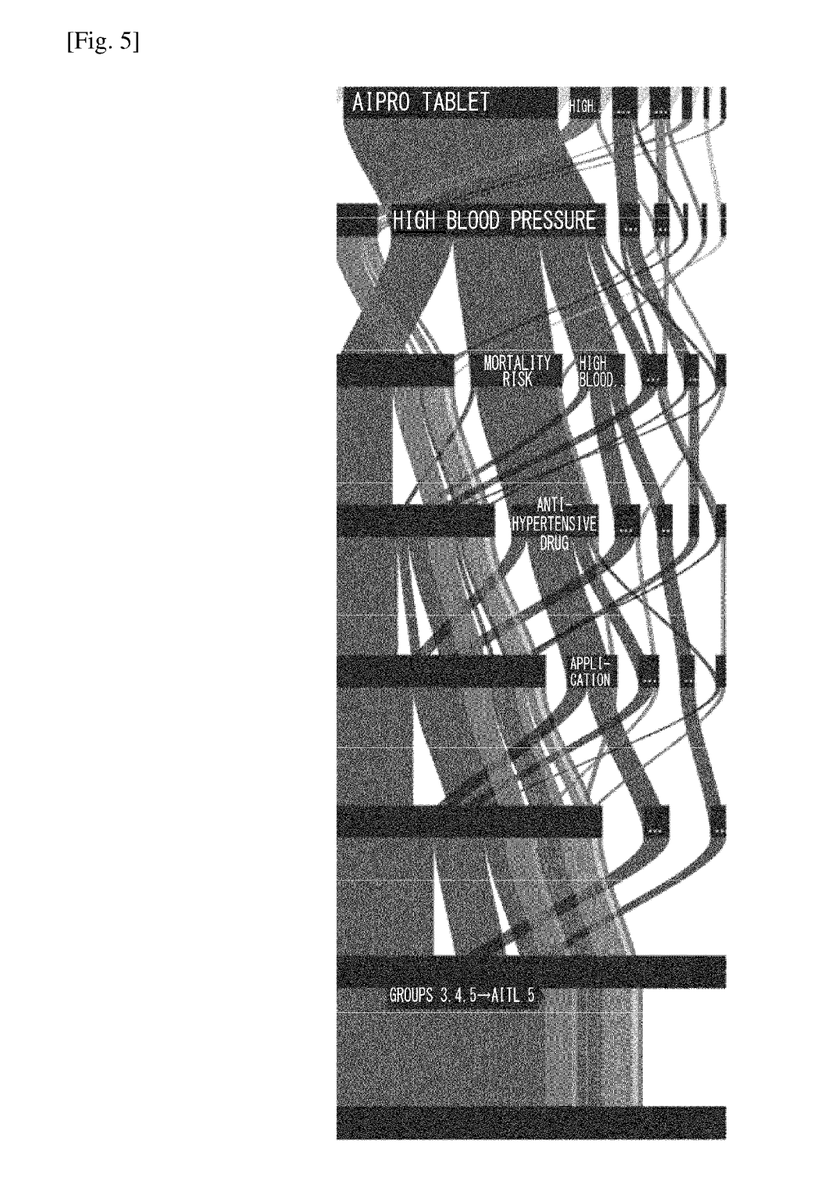
FIG. 5 is a conceptual diagram for describing a registration order of keywords by a group of persons who are not persons having good results.

FIG. 5 is a conceptual diagram for describing a registration order of keywords by a group of persons who are not persons having good results. When FIG. 4 and FIG. 5 are compared, it is found that while the persons having good results have regularity in an appearance order of the keywords in the conversation, the order for the group of persons who are not persons having good results is not constant even though the keywords appear. That is, it is found that when a certain presentation material is explained, the persons having good results have uniformity in the order of using terms and explain in the same context.

INDUSTRIAL APPLICABILITY

This invention can be used in the information and communication industry.

DESCRIPTION OF REFERENCE SIGNS

1 . . . presentation evaluation system
3 . . . voice analysis unit
5 . . . presentation material related information storage unit
7 . . . keyword storage unit
9 . . . related term storage unit
11 . . . evaluation unit
13 . . . grouping unit
15 . . . page extracting unit
17 . . . evaluation keyword extracting unit
19 . . . unused evaluation keyword extracting unit
21 . . . unused evaluation keyword output unit

The invention claimed is:

1. A presentation evaluation system (1) comprising:
   a voice analysis unit (3) that analyzes a content of a conversation;
   a presentation material related information storage unit (5) that stores information related to a presentation material, the information related to the presentation material including information for identifying each page of the presentation material;
   a keyword storage unit (7) that stores a keyword in each page of the presentation material;
   a related term storage unit (9) that stores a related term of the keyword; and
   an evaluation unit (11) that evaluates a content of a conversation analyzed by the voice analysis unit (3) or a person who had the conversation, wherein
   the evaluation unit (11):
      identifies each page of the presentation material based on the information related to the presentation material stored by the presentation material related information storage unit (5);
      reads out a keyword related to an identified page of the presentation material from the keyword storage unit (7);
      reads out a related term of the keyword related to the identified page of the presentation material from the related term storage unit (9);
      uses a count of keywords of each page of the presentation material included in a content of a conversation analyzed by the voice analysis unit (3), a count of related terms of the keyword related to the identified page of the presentation material, a combination of keywords related to the identified page of the presentation material, or a combination of related terms of the keyword related to the identified page of the presentation material;
      obtains an evaluation value for evaluating a conversation content or a person having a conversation by reading out an evaluation value related to the count of keywords of each page of the presentation material included in the content of the conversation analyzed by the voice analysis unit (3), an evaluation value related to the count of related terms of the keyword related to the identified page of the presentation material, an evaluation value related to the combination of keywords related to the identified page of the presentation material, or an evaluation value related to the combination of related terms of the keyword related to the identified page of the presentation material from the storage units to acquire the read evaluation value, and obtains the evaluation value using the read evaluation values by combining the read evaluation values when a plurality of the evaluation values are read out, wherein the combination of keywords related to the identified page of the presentation material is a set of two or more keywords preset among keywords included in the keywords related to the identified page of the presentation material;

determines that the combination of keywords related to the identified page of the presentation material exists when the set of keywords is included in the content of the conversation analyzed by the voice analysis unit (3), wherein the combination of related terms of the keyword related to the identified page of the presentation material is a set of two or more related terms preset among related terms included in the related terms of the keyword related to the identified page of the presentation material;

determines that the combination of related terms of the keyword related to the identified page of the presentation material exists when the set of related terms is included in the content of the conversation analyzed by the voice analysis unit (3); and evaluates the content of the conversation or the person who had the conversation based on the evaluation value for evaluating the conversation content or the person having the conversation, wherein the presentation evaluation system (1) further comprises a grouping unit (13) that obtains an evaluation value for grouping using the count of keywords of each page of the presentation material included in the content of the conversation analyzed by the voice analysis unit (3), the count of related terms, the combination of keywords, or the combination of related terms, and divides persons who had the conversation into groups based on the evaluation value for grouping.

2. The presentation evaluation system (1) according to claim 1, further comprising a page extracting unit (15) that, for a group divided by the grouping unit (13), acquires an evaluation value for each page of the presentation material using the read evaluation value for a page of the presentation material, the read evaluation value being obtained by combining the plurality of read evaluation values when the plurality of evaluation values are read out, and uses the evaluation value for each page of the presentation material to extract a page that allows a group having a higher evaluation value for grouping to have an evaluation value for each page of the presentation material higher than an evaluation value of a group having a lower evaluation value for grouping as an evaluation page that is a page of the presentation material for evaluating the content of the conversation or the person who had the conversation.

3. The presentation evaluation system (1) according to claim 2, wherein the evaluation unit (11) obtains the evaluation value for evaluating the conversation content or the person having the conversation using the count of keywords or the count of related terms in the evaluation page included in the content of the conversation analyzed by the voice analysis unit (3), and evaluates the content of the conversation or the person who had the conversation using the evaluation value for evaluating the conversation content or the person having the conversation.

4. The presentation evaluation system (1) according to claim 3, wherein the keyword storage unit (7) further stores keyword appearance order information related to an appearance order of the keywords and an evaluation value corresponding to the keyword appearance order, and wherein the evaluation unit (11) obtains the evaluation value for evaluating the conversation content or the person having the conversation further using the keyword appearance order information in the evaluation page included in the content of the conversation analyzed by the voice analysis unit (3), and evaluates the content of the conversation or the person who had the conversation using the evaluation value for evaluating the conversation content or the person having the conversation.

5. The presentation evaluation system (1) according to claim 4, further comprising:

in a group having a highest count of keywords, a highest count of related terms, a highest count of combinations of keywords, or a highest count of combinations of related terms of each page of the presentation material, among the groups divided by the grouping unit (13), an evaluation keyword extracting unit (17) that extracts a keyword used related to the evaluation page as an evaluation keyword;

an unused evaluation keyword extracting unit (21) that extracts an unused evaluation keyword that is a keyword included in the content of the conversation analyzed by the voice analysis unit (3) and is not the evaluation keyword; and an unused evaluation keyword output unit (23) that outputs the unused evaluation keyword extracted by the unused evaluation keyword extracting unit (21).

6. A non-transitory computer-readable medium encoded with a computer program, where when the computer program is executed, the computer program causes the computer to function as a presentation evaluation system (1), the presentation evaluation system (1) comprising:

a voice analysis unit (3) that analyzes a content of a conversation;

a presentation material related information storage unit (5) that stores information related to a presentation material, the information related to the presentation material including information for identifying each page of the presentation material;

a keyword storage unit (7) that stores a keyword in each page of the presentation material;

a related term storage unit (9) that stores a related term of the keyword; and an evaluation unit (11) that evaluates a content of a conversation analyzed by the voice analysis unit (3) or a person who had the conversation, wherein the evaluation unit (11):

identifies each page of the presentation material based on the information related to the presentation material stored by the presentation material related information storage unit (5);

reads out a keyword related to an identified page of the presentation material from the keyword storage unit (7);

reads out a related term of the keyword related to the identified page of the presentation material from the related term storage unit (9);

uses a count of keywords of each page of the presentation material included in a content of a conversation analyzed by the voice analysis unit (3), a count of related terms of the keyword related to the identified page of the presentation material, a combination of keywords related to the identified page of the presentation material, or a combination of related terms of the keyword related to the identified page of the presentation material;

obtains an evaluation value for evaluating a conversation content or a person having a conversation by reading out an evaluation value related to the count of keywords of each page of the presentation material included in the content of the conversation analyzed by the voice analysis unit (3), an evaluation value related to the count of related terms of the keyword related to the identified page of the presentation material, an evaluation value related to the combination of keywords related to the identified page of the presentation material, or an evaluation value related to the combination of related terms of the keyword related to the identified page of the presentation material from the storage units to acquire the read evaluation value, and obtains the evaluation value using the read evaluation values by combining the read evaluation values when a plurality of the evaluation values are read out, wherein the combination of keywords related to the identified page of the presentation material is a set of two or more keywords preset among keywords included in the keywords related to the identified page of the presentation material;

determines that the combination of keywords related to the identified page of the presentation material exists when the set of keywords is included in the content of the conversation analyzed by the voice analysis unit (3), wherein the combination of related terms of the keyword related to the identified page of the presentation material is a set of two or more related terms preset among related terms included in the related terms of the keyword related to the identified page of the presentation material;

determines that the combination of related terms of the keyword related to the identified page of the presentation material exists when the set of related terms is included in the content of the conversation analyzed by the voice analysis unit (3); and evaluates the content of the conversation or the person who had the conversation based on the evaluation value for evaluating a conversation content or a person having a conversation, wherein the presentation evaluation system (1) further comprises a grouping unit (13) that obtains an evaluation value for grouping using the count of keywords of each page of the presentation material included in the content of the conversation analyzed by the voice analysis unit (3), the count of related terms, the combination of keywords, or the combination of related terms, and divides persons who had the conversation into groups based on the evaluation value for grouping.

* * * * *